United States Patent [19]

Ehrenfreund et al.

[11] 4,321,276
[45] Mar. 23, 1982

[54] PHENYLUREAS

[75] Inventors: Josef Ehrenfreund, Allschwil; Achim Roloff, Rheinfelden, both of Switzerland

[73] Assignee: Ciba-Geigy Corporation, Ardsley, N.Y.

[21] Appl. No.: 254,337

[22] Filed: Apr. 14, 1981

[30] Foreign Application Priority Data

Apr. 17, 1980 [CH] Switzerland .................. 2984/80
Oct. 8, 1980 [CH] Switzerland .................. 7508/80

[51] Int. Cl.³ .................. C07C 127/22; A01N 9/20
[52] U.S. Cl. .................. 424/322; 564/44
[58] Field of Search .................. 564/44; 424/322

[56] References Cited

U.S. PATENT DOCUMENTS 4,162,330 7/1979 Ehrenfreund .................. 564/44 X
4,262,020 4/1981 Ehrenfreund .................. 424/322

OTHER PUBLICATIONS

Hajjar et al., CA 91:51064k (1979).

*Primary Examiner*—Thomas A. Waltz
*Attorney, Agent, or Firm*—Frederick H. Rabin

[57] ABSTRACT

The invention relates to novel substituted N-ethynyl-phenyl-N'-benzoylureas of the formula

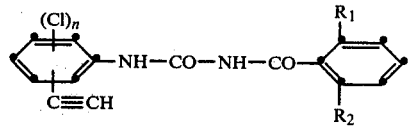

wherein $R_1$ is fluorine, chlorine, bromine, methoxy or methyl, $R_2$ is hydrogen, fluorine, chlorine, bromine, methoxy or methyl, and n is 0 or 1, while the ethynyl radical —C≡CH is in the 3- or 4-position, to methods of obtaining these compounds and to compositions containing them for use in pest control, especially for controlling insects that attack plants and animals. The novel compounds have a pronounced ovolarvicidal, especially ovicidal, activity against plant-destructive insects.

12 Claims, No Drawings

PHENYLUREAS

The present invention relates to novel substituted N-ethynylphenyl-N'-benzoylureas, to the production thereof, and to the use thereof in pest control.

The substituted N-ethynylphenyl-N'-benzoylureas of this invention have the formula

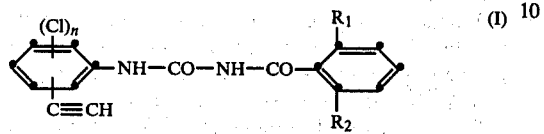

wherein $R_1$ is fluorine, chlorine, bromine, methoxy or methyl, $R_2$ is hydrogen, fluorine, chlorine, bromine, methoxy or methyl, and n is 0 or 1, whilst the ethynyl radical —C≡CH is in the 3- or 4-position.

Preferred compounds of the formula I on account of their pesticidal activity are those wherein the ethynyl radical —C≡CH is in the 4-position, and those wherein $R_1$ is fluorine, chlorine, bromine or methyl, $R_2$ is hydrogen, fluorine or chlorine and n is 0. Valuable compounds of the formula I on account of their biological activity are also those wherein $R_1$ is fluorine or chlorine and $R_2$ is fluorine. Particularly effective compounds of the formula I are those wherein $R_1$ is chlorine or methyl and $R_2$ is hydrogen.

The compounds of the formula I can be obtained by methods which are known per se (cf. inter alia German Offenlegungsschriften 2 123 236, 2 601 780, and European patent application No. 13414).

Thus, for example, a compound of the formula I can be obtained by (a) reacting a compound of the formula II

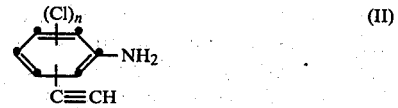

with a compound of the formula III

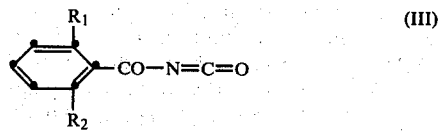

or (b) reacting a compound of the formula IV

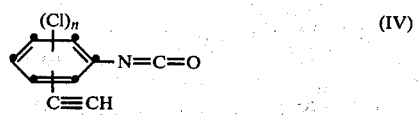

with a compound of the formula V

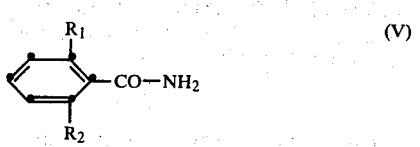

or (c) reacting a compound of the formula II with a compound of the formula VI

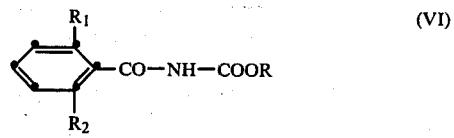

In the formulae II, III, IV, V and VI above, $R_1$, $R_2$ and n are as defined for formula I and R is a $C_1$-$C_8$alkyl radical which can be substituted by halogen.

The above processes (a), (b) and (c) can preferably be carried out under normal pressure and in the presence of an organic solvent or diluent. Examples of suitable solvents or diluents are: ethers and ethereal compounds, such as diethyl ether, dipropyl ether, dibutyl ether, dioxane, dimethoxyethane and tetrahydrofurane; N,N-dialkylated carboxamides; aliphatic, aromatic and halogenated hydrocarbons, especially benzene, toluene, xylene, chloroform, methylene chloride, carbon tetrachloride and chlorobenzene; nitriles such as acetonitrile or propionitrile; dimethyl sulfoxide; and ketones, e.g. acetone, methyl ethyl ketone, methyl isopropyl ketone and methyl isobutyl ketone. Process (a) is normally carried out in the temperature range from −10° to 100° C., preferably from 15° to 25° C., if desired in the presence of an organic base, e.g. triethylamine. Process (b) is carried out in the temperature range from 0° to 120° C., preferably at the boiling point of the solvent employed, and, if desired, in the presence of an organic base such as pyridine, and/or with the addition of an alkali metal or alkaline earth metal, preferably sodium. For process (c), i.e. for the reaction of the urethane of the formula VI with the aminophenylacetylene of the formula II, at a temperature range from about 60° to the boiling point of the reaction mixture is preferred, and the solvent employed is preferably an aromatic hydrocarbon such as toluene, xylene, chlorobenzene etc.

The starting materials of the formulae II, III, IV, V and VI above are known or, where new, can be prepared by methods analogous to known ones. Accordingly, the aminophenylacetylenes of the formula II can be obtained by reacting initially 1,1-dimethyl-2-propyn-1-ol in the presence of a suitable catalyst, in alkaline medium, with the corresponding substituted 2- or 4-halo-nitrobenzenes or -anilines (the amino group of which is protected), accompanied by dehydrohalogenation (cf. Tetrahedron Letters 1975, 4467; J. Organomet. Chem. 93/1973, 253 and 259; Italian patent specification 1 006 879; and U.S. patent specification 4 128 588). The resultant compounds of the formula VII below are then reacted under alkaline conditions, with the elimination of acetone, to give compounds of formula VIII (cf. J. Org. Chem. 44/1979, 1233; German Offenlegungsschrift 2 905 507):

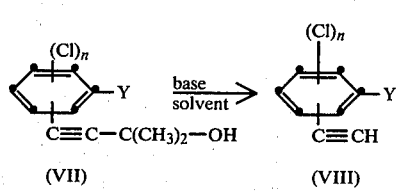

In the formulae VII and VIII above, n is as defined above, the ethynyl radical is in the 3- or 4-position, and Y is a nitro group or a protected amino group. The compound of the formula VIII can then be converted by conventional methods into a compound of the formula II by reduction of the nitro group or removal of the protective group.

3-Aminophenylacetylene and 4-aminophenylacetylene of formula II are known compounds (cf. J. Org. Chem. 44/1979, 1233 and 3671, and Tetrahedron Letters 5/1979, 351).

The benzamides of the formula V and the benzoylisocyanates of the formula III can be obtained, inter alia, starting from corresponding nitriles in accordance with the following reaction scheme (cf. J. Agr. Food Chem 21, 348 and 993, 1973):

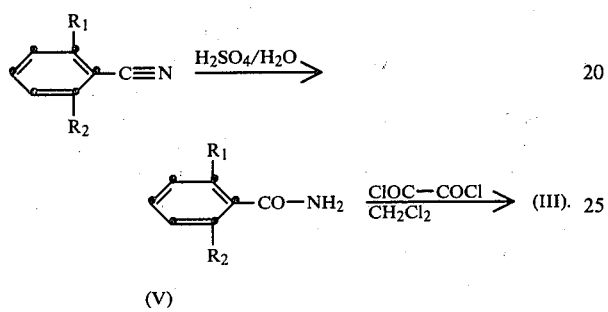

The phenylisocyanates of the formula IV can be prepared e.g. by reacting the corresponding aminophenylacetylenes of the formula II with phosgene by conventional methods. The starting benzamides of the formula V mentioned above are for the most part known (cf. Beilstein "Handbuch der organischen Chemie", Vol. 9, p. 336). The urethanes of the formula VI can be obtained in a manner known per se by reacting a benzoylisocyanate of the formula III with a corresponding alcohol or by reacting a benzamide of the formula V, in the presence of a base, with a corresponding ester of chloroformic acid.

It is already known that specific substituted N-phenyl-N'-benzoylureas possess pesticidal and insecticidal properties (cf. German Offenlegungsschriften 2,123,236; 2,531,279; 2,601,780; 2,726,684; 2,801,316 and 2,820,696; European patent applications 1203 and 4030; and U.S. Pat. No. 4,089,975). Substituted N-phenyl-N'-2,6-dichlorobenzoylureas which are said to have insecticidal properties are known from J. Agr. Food Chem. 21, 348 ff., (1973), and 24, 134 (1976).

Surprisingly, it has been found that in contrast to the above compounds, the compounds of this invention have excellent pesticidal activity while being well tolerated by plants and having low mammalian toxicity. They are suitable in particular for controlling pests that attack plants and animals.

In particular, the compounds of the formula I are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera.

In addition to their very advantageous action against flies, e.g. Musca domestica, and mosquito larvae, the compounds of the formula I are also suitable for controlling plant-destructive feeding insects in ornamentals and crops of useful plants, especially in cotton (e.g. against Spodoptera littoralis and Heliothis virescens) and in fruit and vegetables (e.g. against *Laspeyresia pomonella, Leptinotarsa decemlineata* and *Pieris brassicae*). The pronounced ovicidal and ovolarvicidal action of the compounds of the formula I is to be singled out for special mention. When compounds of the formula I are ingested with the feed by adult insects, then reduced oviposition and/or a reduced hatching rate is observed in many pests, especially in Coleoptera, e.g. *Anthonomus grandis.*

Furthermore, the compounds of the formula I are suitable for controlling ectoparasites in domestic animals and productive livestock, e.g. by treating animals, cowsheds, barns, stables etc., and pastures.

The activity of the compounds of the formula I and of the compositions containing them can be substantially broadened and adapted to prevailing circumstances by addition of other insecticides and/or acaricides. Examples of suitable additives include: organophosphorus compounds, nitrophenols and derivatives thereof, formamides, ureas, pyrethroids, carbamates, chlorinated hydrocarbons, and Bacillus thuringiensis preparations.

Compounds of formula I are also combined with particular advantage with substances which exert a pesticidally potentiating action. Examples of such compounds include: piperonyl butoxide, propynyl ethers, propynyl oximes, propynyl carbamates and propynyn phosphates, 2-(3,4-methylenedioxyphenoxy)-3,6,9-trioxaundecane or S,S,S-tributylphosphorotrithioate.

The compounds of formula I may be used as pure active ingredient or together with suitable carriers and/or adjuvants. Suitable carriers and adjuvants can be solid or liquid and correspond to the substances conventionally used in the art of formulation, for example natural or regenerated substances, solvents, dispersants, wetting agents, thickeners, binders and/or fertilisers. For application, the compounds of the formula I may be processed to dusts, emulsifiable concentrates, granules, dispersions, sprays, to solutions or suspensions, in the conventional formulation commonly employed in application technology. In addition, cattle dips and spray races, in which aqueous preparations are used, may also be mentioned. These formulations are particularly suitable for controlling pests which are parasites of animals.

The compositions of the present invention are prepared in known manner by homogeneously mixing and/or grinding compounds of formula I with the suitable carriers, if desired with the addition of dispersants or solvents which are inert to the active ingredients.

The compounds of formula I may be processed to the following formulations:

Solid formulations:
dusts, tracking powders and granules (coated granules, impregnated granules and homogeneous granules).

Liquid formulations:
(a) water-dispersible active ingredient concentrates: wettable powders, pastes and emulsions;
(b) solutions.

The content of active ingredient in the above described compositions is between 0.1% and 95%.

The compounds (active ingredients) of formula I can, for example, be formulated as follows (throughout the present specification all parts and percentages are by weight):

Dust

The following substances are used to formulate (a) a 5% and (b) 2% dust:

(a) 5 parts of active ingredient,
95 parts of talc;
(2) parts of active ingredient,
1 part of highly disperse silicic acid, 97 parts of talc The active ingredients are mixed and ground with the carriers.

Granules

The following substances are used to formulate 5% granules:
5 parts of active ingredient,
0.25 part of epoxidised vegetable oil,
0.25 part of cetyl polyglycol ether,
3.50 parts of polyethylene glycol,
91 parts of kaolin (particle size 0.3–0.8 mm).

The active ingredient is mixed with the epoxidised vegetable oil and the mixture is dissolved in 6 parts of acetone; the polyethylene glycol and cetyl polyglycol ether are then added. The resultant solution is sprayed on kaolin, and the acetone is subsequently evaporated in vacuo.

Wettable Powders

The following constituents are used to formulate (a) a 40%, (b) and (c) a 25%, and (d) a 10% wettable powder:
(a) 40 parts of active ingredient,
5 parts of sodium lignosulfonate,
1 part of sodium dibutylnaphthalenesulfonate,
54 parts of silicic acid;
(b) 25.0 parts of active ingredient,
4.5 parts of calcium lignosulfonate,
1.9 parts of Champagne chalk/hydroxyethyl cellulose mixture (1:1),
1.5 parts of sodium dibutylnaphthalenesulfonate,
19.5 parts of silicic acid,
19.5 parts of Champagne chalk,
28.1 parts of kaolin;
(c) 25.0 parts of active ingredient,
2.5 parts of isooctylphenoxy-polyoxyethylene ethanol,
1.7 parts of Champagne chalk/hydroxyethyl cellulose mixture (1:1),
8.3 parts of sodium aluminium silicate,
16.5 parts of kieselgur,
46.0 parts of kaolin,
(d) 10 parts of active ingredient,
3 parts of a mixture of the sodium salts of saturated fatty alcohol sulfates,
5 parts of naphthlenesulfonic acid/formaldehyde concensate,
82 parts of kaolin.

The active ingredients are homogeneously mixed with the additives in suitable mixers and the mixture is then ground in appropriate mills and rollers. Wettable powders are obtained which can be diluted with water to give suspensions of the desired concentration.

Emulsifiable Concentrate

The following substances are used to formulate a 10% emulsifiable concentrate:
10 parts of active ingredient,
3.4 parts of epoxidised vegetable oil,
3.4 parts of a combination emulsifier consisting of fatty alcohol polyglycol ether and alkylarylsulfonate/-calcium salt,
40 parts of dimethyl formamide,
43.2 parts of xylene.

By diluting such a concentrate with water it is possible to obtain emulsions of the required concentration.

Spray

The following ingredients are used to formulate a 5% spray:
5 parts of active ingredient,
1 part of epoxidised vegetable oil,
94 part of ligroin (boiling range 160°–190° C.).

The invention is further illustrated by the following Examples.

EXAMPLE 1

With stirring, 3.2 g of 2,6-difluorobenzoylisocyanate are added dropwise to a ready prepared mixture of 2 g of 4-aminophenylacetylene in 20 ml of absolute ether. The precipitate is filtered with suction after 2 hours and recrystallised from ethanol, yielding N-(4-ethynylphenyl)-N'-(2,6-difluorobenzoyl)urea with a melting point of 213°–217° C. (Compound 1).

The following compounds of the formula I are prepared in analogous manner:

| Compound | $R_1$ | $R_2$ | Position of the ethynyl group | $(Cl)_n$ | melting point [°C.] |
|---|---|---|---|---|---|
| 1  | F    | F  | 4-C≡CH | n = 0 | 213–217 |
| 2  | Cl   | H  | 4-C≡CH | n = 0 | 189–192 |
| 3  | F    | H  | 4-C≡CH | n = 0 | 213–214.5 |
| 4  | F    | Cl | 4-C≡CH | n = 0 | 158–161 |
| 5  | Cl   | Cl | 4-C≡CH | n = 0 | 215–217 |
| 6  | Br   | H  | 4-C≡CH | n = 0 | 191–193 |
| 7  | CH₃  | H  | 4-C≡CH | n = 0 | 188–189.5 |
| 8  | CH₃O | Cl | 4-C≡CH | n = 0 | 184–185 |
| 9  | F    | H  | 4-C≡CH | 3-Cl | 220 |
| 10 | F    | F  | 4-C≡CH | 3-Cl | 220–223 |
| 11 | Cl   | H  | 4-C≡CH | 3-Cl | 202–205 |
| 12 | Cl   | F  | 4-C≡CH | 3-Cl | 199–201 |
| 13 | Cl   | Cl | 4-C≡CH | 3-Cl | 208–212 |
| 14 | Cl   | H  | 3-C≡CH | 4-Cl | 205–207 |
| 15 | F    | F  | 3-C≡CH | 4-Cl | 242–244 |
| 16 | F    | Cl | 3-C≡CH | 4Cl | 210–213 |
| 17 | CH₃  | H  | 3-C≡CH | 4-Cl | 222–223 |
| 18 | F    | F  | 3-C≡CH | n = 0 | 173–176 |
| 19 | F    | Cl | 3-C≡CH | n = 0 | 225 |
| 20 | F    | H  | 3-C≡CH | n = 0 | 165–168 |
| 21 | Cl   | Cl | 3-C≡CH | n = 0 | 219–221 |
| 22 | Cl   | H  | 3-C≡CH | n = 0 | 185–188 |
| 23 | Br   | H  | 3-C≡CH | n = 0 | 174–176 |
| 24 | CH₃  | H  | 3-C≡CH | n = 0 | 181–182 |
| 25 | F    | Cl | 4-C≡CH | 2-Cl |  |
| 26 | Cl   | H  | 4-C≡CH | 2-Cl |  |
| 27 | Cl   | Cl | 4-C≡CH | 2-Cl |  |

EXAMPLE 2

Action Against *Musca domestica*

50 g of freshly prepared CSMA nutrient substrate for maggots were charged into beakers. A specific amount of a 1% acetonic solution of the respective active ingredient was pipetted onto the nutrient substrate present in the beakers. The substrate was then thoroughly mixed and the acetone subsequently allowed to evaporate over a period of at least 20 hours.

Then 25 one-day-old maggots of *Musca domestica* were put into each of the beakers containing the treated nutrient substrate for testing with each active ingredient at one of its given concentrations. After the maggots had pupated, the pupae were separated from the substrate by flushing them out with water and then deposited in containers closed with a perforated top.

Each batch of flushed out pupae was counted to determine the toxic effect of the active ingredient on the maggot development. A count was then made after 10 days of the number of flies which had hatched out of the pupae.

The compounds of Example 1 were very effective in this test.

EXAMPLE 3

Action Against *Lucilia sericata*

1 ml of an aqueous formulation containing 0.5% of test substance was added at 50° C. to 9 ml of a culture medium. Then about 30 freshly hatched *Lucilia sericata* larvae were added to the culture medium, and the insecticidal action was determined after 48 and 96 hours by evaluating the mortality rate. In this test, compounds of Example 1 were very effective against *Lucilia sericata*.

EXAMPLE 4

Action Against *Aedes aegypti*

Active ingredient concentrations of 10,5 and 1 ppm respectively were obtained by pipetting a specific amount of a 0.1% solution in acetone of each compound to be tested onto the surface of 150 ml of water in each of a number of beakers. After the acetone had evaporated, 30 to 40 three-day-old larvae of *Aedes aegypti* were put into each of the beakers containing the active ingredient solution. Mortality counts were made after 1, 2 and 5 days.

In this test, compounds of Example 1 were very effective against *Aedes aegypti*.

EXAMPLE 5

Insecticidal Stomach Poison Action

Potted cotton plants having a height of about 25 cm were sprayed with aqueous emulsions containing each compound to be tested in concentrations of 800, 400, 200, 100 and 50 ppm. After the spray coating has dried, the cotton plants were populated with *Spodoptera littoralis* and *Heliothis virescens* larvae in the $L_3$-stage. The test was carried out at 24° C. and 60% relative humidity. The percentage mortality was determined after 120 hours.

EXAMPLE 6

Action Against *Spodoptera littoralis* and *Heliothis virescens* (Larvae and Eggs)

Three cotton plants having a height of about 15–20 cm and reared in pots were treated with a sprayable liquid preparation of the compound to be tested. After the spray coating had dried, the potted plants were placed in a metal container having a capacity of about 20 liters and covered with a glass plate. The humidity in the interior of the covered container was regulated such that no water of condensation formed. Direct light falling on the plants was avoided. The three plants were then infested altogether with:

(a) 50 larvae of *Spodoptera littoralis* or *Heliothis virescens* in the $L_1$-stage;

(b) 20 larvae of *Spodoptera littoralis* or *Heliothis virescens* in the $L_3$-stage;

(c) 2 egg deposits of *Spodoptera littoralis* or *Heliothis virescens*.

Two leaves of each plant were put into a plexiglass cylinder sealed at both ends with muslin. Two egg deposits of Spodoptera, or a part of a cotton leaf with eggs of Heliothis deposted thereon, were added to the leaves sealed in the cylinder.

Evaluation in comparison to untreated controls was made after 4 to 5 days, taking into account the following criteria:

(a) the number of still living larvae, (b) inhibition of larval development and shedding, (c) feeding damage (shredding and perforation damage), (d) hatching rate (number of larvae hatched from the eggs).

In this test, the compounds of Example 1 exhibited good overall activity.

EXAMPLE 7

Ovicidal Action Against *Spodoptera littoralis*

Eggs of *Spodoptera littoralis* deposited on filter paper were cut out of the paper and immersed in solutions of each compound to be tested in a 1:1 mixture of acetone-water. The solutions contained 400 and 100 ppm respectively of active ingredient. The treated deposits were then removed from this mixture and kept in plastic dishes at 21° C. and 60% humidity. The hatching rate, i.e. the number of larvae which had developed from the treated eggs, was determined after 3 to 4 days.

EXAMPLE 8

Ovicidal Action Against *Heliothis virescens*

Corresponding amounts of a wettable powder formulation containing 25% by weight of the compound to be tested were mixed with sufficient water to produce aqueous emulsions of increasing concentration. One-day-old egg deposits of Heliothis on cellophane were immersed in these emulsions for 3 minutes and then collected by suction on round filters. The treated deposits were placed in petri dishes and kept in the dark. The hatching rate in comparison with untreated controls was determined after 6 to 8 days. Evaluation was made by determining the minimum concentration necessary for 100% kill of the eggs.

In this test the compounds of Example 1 exhibited very good ovicidal action against the tested pests.

EXAMPLE 9

Action Against *Laspeyresia pomonella* (Eggs)

Egg deposits of *Laspeyresia pomonella* not more than 24 hours old were immersed, on filter paper, for 1 minute in acetonic aqueous solutions containing 800, 50 and 3 ppm respectively of the compound to be tested. After the solution had dried, the eggs were placed in petri dishes and kept at a temperature of 28° C. The percentage of larvae hatched from the treated eggs was determined after 6 days in comparison with untreated controls.

Biological Results

The results of the biological tests carried out with the compounds of the invention in accordance with foregoing Examples are reported in the following Table. Evaluation of the tests in terms of percentage mortality was made using the following rating:

| Compound | Pesticidal activity | | | |
|---|---|---|---|---|
| | Spodoptera larvea (Example 5) | Heliothis larvae (Example 5) | Laspeyresia eggs (Example 9) | Spodoptera eggs (Example 7) |
| 1 | B | C | A | C |
| 2 | B | B | B | — |
| 3 | C | F | F | E |
| 4 | B | B | A | E |
| 5 | C | E | F | E |
| 6 | B | D | A | — |
| 7 | B | F | A | E |
| 8 | C | E | — | — |
| 10 | E | E | — | — |
| 11 | E | E | — | — |
| 12 | F | F | — | — |
| 13 | D | F | — | — |
| 14 | E | E | — | — |
| 15 | E | E | — | — |
| 16 | E | E | — | — |
| 17 | E | E | — | — |
| 18 | B | D | — | — |
| 19 | E | F | — | — |
| 20 | B | C | F | E |
| 21 | D | F | — | — |
| 22 | D | F | — | — |
| 23 | E | E | — | — |
| 24 | C | F | F | E |

A: 80–100% mortality at a concentration of 12.55 ppm of the tested compound
B: 80–100% mortality at a concentration of 50 ppm of the tested compound
C: 80–100% mortality at a concentration of 100 ppm of the tested compound
D: 80–100% mortality at a concentration of 200 ppm of the tested compound
E: 80–100% mortality at a concentration of 400 ppm of the tested compound
F: less than 80% mortality at a concentration of 800 ppm of the tested compound
—: not tested.

What is claimed is:

1. A compound of the formula

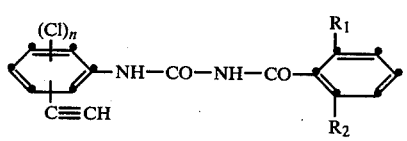

wherein $R_1$ is fluorine, chlorine, bromine, methoxy or methyl, $R_2$ is hydrogen, fluorine, chlorine, bromine, methoxy or methyl, and n is 0 or 1, whilst the ethynyl radical —C≡CH is in the 3- or 4-position.

2. A compound according to claim 1, wherein the ethynyl radical is in the 4-position.

3. A compound according to claim 1, wherein $R_1$ is fluorine, chlorine, bromine or methyl, $R_2$ is hydrogen, fluorine or chlorine, and n is 0, whilst the ethynyl radical —C≡CH is in the 4-position.

4. A compound according to claim 3, wherein $R_1$ is fluorine or chlorine and $R_2$ is fluorine.

5. A compound according to claim 3, wherein $R_1$ is chlorine or methyl and $R_2$ is hydrogen.

6. The compound according to claim 4 of the formula

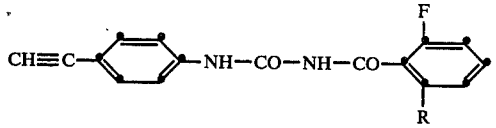

7. The compound according to claim 5 of the formula

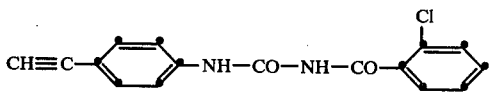

8. The compound according to claim 4 of the formula

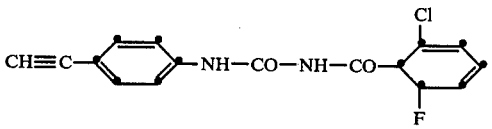

9. The compound according to claim 5 of the formula

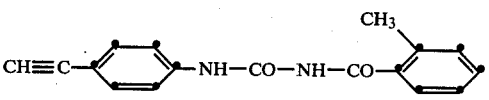

10. A insecticidal composition which contains as the active ingredient a insecticidally effective amount of a compound according to one of claims 1 to 9 together with suitable carriers and/or other adjuvants therefor.

11. A method for combating insects, which method comprises applying to said insects or to a locus derived to be protected from said insects an insecticidally effective amount of a compound according to one of claims 1 to 9.

12. A method according to claim 11 for combating plant-destructive insects, wherein the compound is applied as ovicide.

* * * * *